US00PP22670P2

(12) United States Plant Patent
Bauer

(10) Patent No.: US PP22,670 P2
(45) Date of Patent: Apr. 17, 2012

(54) ***COREOPSIS* PLANT NAMED 'SUNSET STRIP'**

(50) Latin Name: ***Coreopsis* hybrid**
Varietal Denomination: Sunset Strip

(75) Inventor: Patricia M. Bauer, Lucinda, PA (US)

(73) Assignee: Itsaul Plants LLC, Alpharetta, GA (US)

( * ) Notice: Subject to any disclaimer, the term of this patent is extended or adjusted under 35 U.S.C. 154(b) by 0 days.

(21) Appl. No.: 12/930,920

(22) Filed: Jan. 20, 2011

(51) Int. Cl.
*A01H 5/00* (2006.01)

(52) U.S. Cl. ..... Plt./417
(58) Field of Classification Search ..... Plt./417
See application file for complete search history.

*Primary Examiner* — Annette Para
(74) *Attorney, Agent, or Firm* — Penny J. Aguirre

(57) ABSTRACT

A new cultivar of *Coreopsis verticillata* named 'Sunset Strip' characterized its large inflorescences that are golden yellow in color with dark orange centers with the dark orange coloration of the ray florets spreading along the veins towards the end of the petals that is especially distinct in fall, its height of 45 to 50 cm and an average spread of 61 cm, its continuous bloom from June until frost, its vigorous growth habit with good growth under greenhouse conditions in winter, and its cold hardiness to at least U.S.D.A. Zone 5.

2 Drawing Sheets

Botanical classification: *Coreopsis* hybrid.
Variety denomination: 'Sunset Strip'.

BACKGROUND OF THE INVENTION

The present invention relates to a new and distinct cultivar of *Coreopsis* plant, botanically known as *Coreopsis verticillata* 'Sunset Strip' and will be referred to hereinafter by its cultivar name, 'Sunset Strip'. The new cultivar of *Coreopsis* is an herbaceous perennial grown for landscape and container use.

The new invention arose as a naturally occurring seedling in the Inventor's garden in Lucinda, Pa. in summer of 2007. The parent plants of 'Sunset Strip' are unknown.

Asexual reproduction of the new cultivar was first accomplished under the direction of the Inventor in Alpharetta, Ga. in November of 2009. The characteristics of this cultivar have been determined to be stable and are reproduced true to type in successive generations.

SUMMARY OF THE INVENTION

The following traits have been repeatedly observed and are determined to be the characteristics of the new cultivar. These attributes in combination distinguish 'Sunset Strip' as unique from all *Coreopsis* cultivars and species known to the Inventor.

1. 'Sunset Strip' exhibits composite inflorescences with ray florets that are golden yellow in color with dark orange centers and dark orange coloration spreads along the veins and towards the end of the petals. The spreading of dark orange coloration towards the petal tips is most distinct in fall.
2. 'Sunset Strip' exhibits inflorescences that are large in size in comparison to what is typical for other cultivars of *Coreopsis verticillata.*
3. 'Sunset Strip' has proven to be hardy at least in U.S.D.A. Zone 5.
4. 'Sunset Strip' blooms continuously from June until frost in Pennsylvania.
5. 'Sunset Strip' exhibits a height of 45 to 50 cm (18 to 20 inches) and an average spread of 61 cm (24 inches).

6. 'Sunset Strip' exhibits a vigorous growth habit and grows well under greenhouse conditions in winter.

'Sunset Strip' can be most closely compared to *Coreopsis* 'Sienna Sunset' (U.S. Plant Pat. No. 20,470) and *Coreopsis* 'Route 66' (U.S. Plant Pat. No. 20,609). 'Sienna Sunset' is similar to 'Sunset Strip' in having threadlike foliage and in having inflorescences that are orange in color. 'Sienna Sunset' differs from 'Sunset Strip' in having ray florets that range from orange to peach in color, lack a center eye (solid in color), in being wider in plant spread and in being slow growing in the greenhouse in winter. 'Route 66' is similar to 'Sunset Strip' in inflorescence size, in having ray florets with a dark colored eye that spreads toward the petal tips, and in growing well under greenhouse conditions in winter. 'Route 66' differs from 'Sunset Strip' in having ray florets that are yellow in color with a burgundy eye that spreads more extensively to the petal tips in fall, and in having a taller plant height.

BRIEF DESCRIPTION OF THE DRAWING

The accompanying colored photographs illustrate the overall appearance and distinct characteristics of the new *Coreopsis* as grown in Alpharetta, Ga.

The photograph in FIG. 1 was taken of plants 3-months in age from a 72-inch plug as grown in one-gallon containers in an open greenhouse and provides a view of the inflorescence color in fall.

Figure 1:
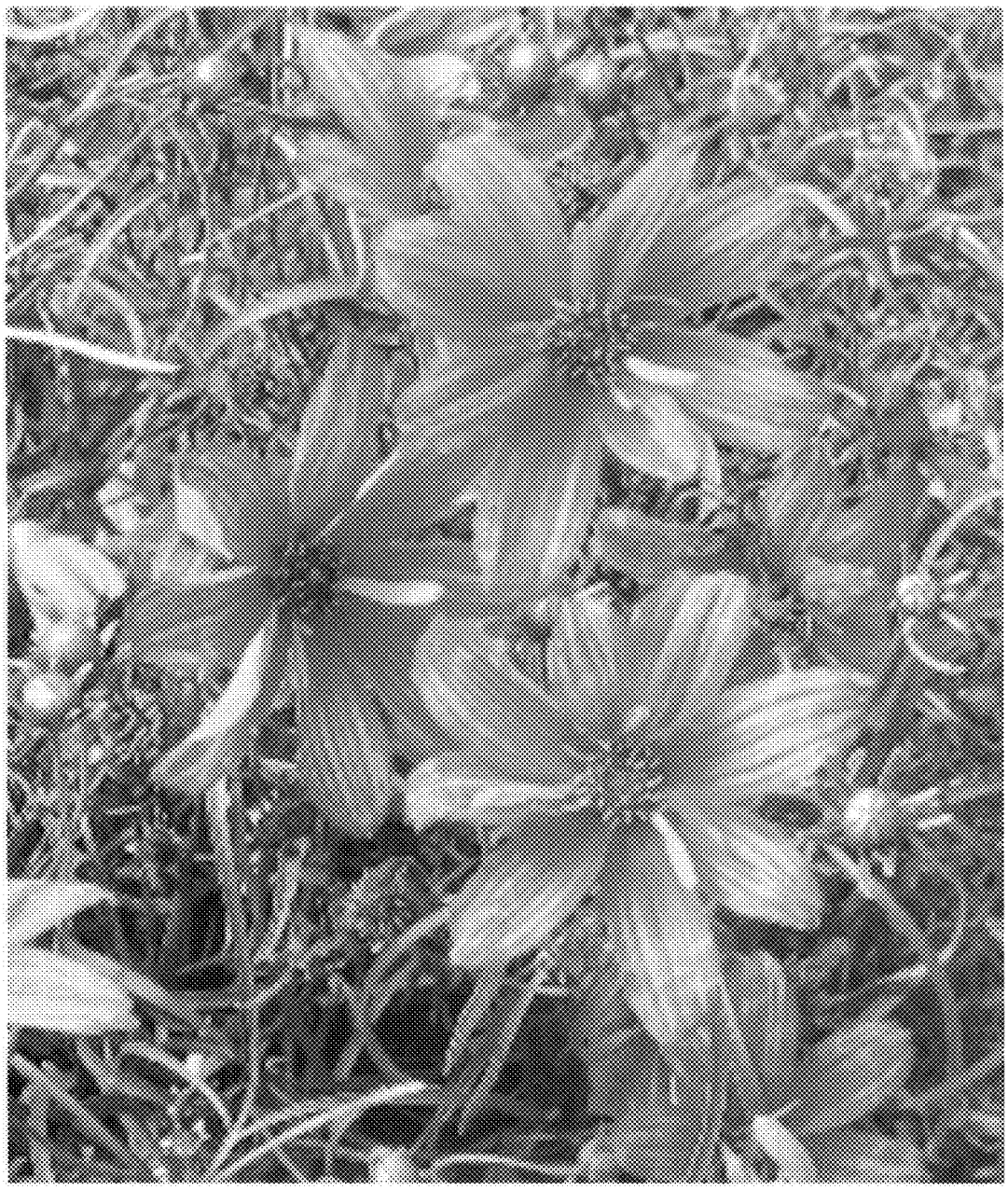
Figure 2:
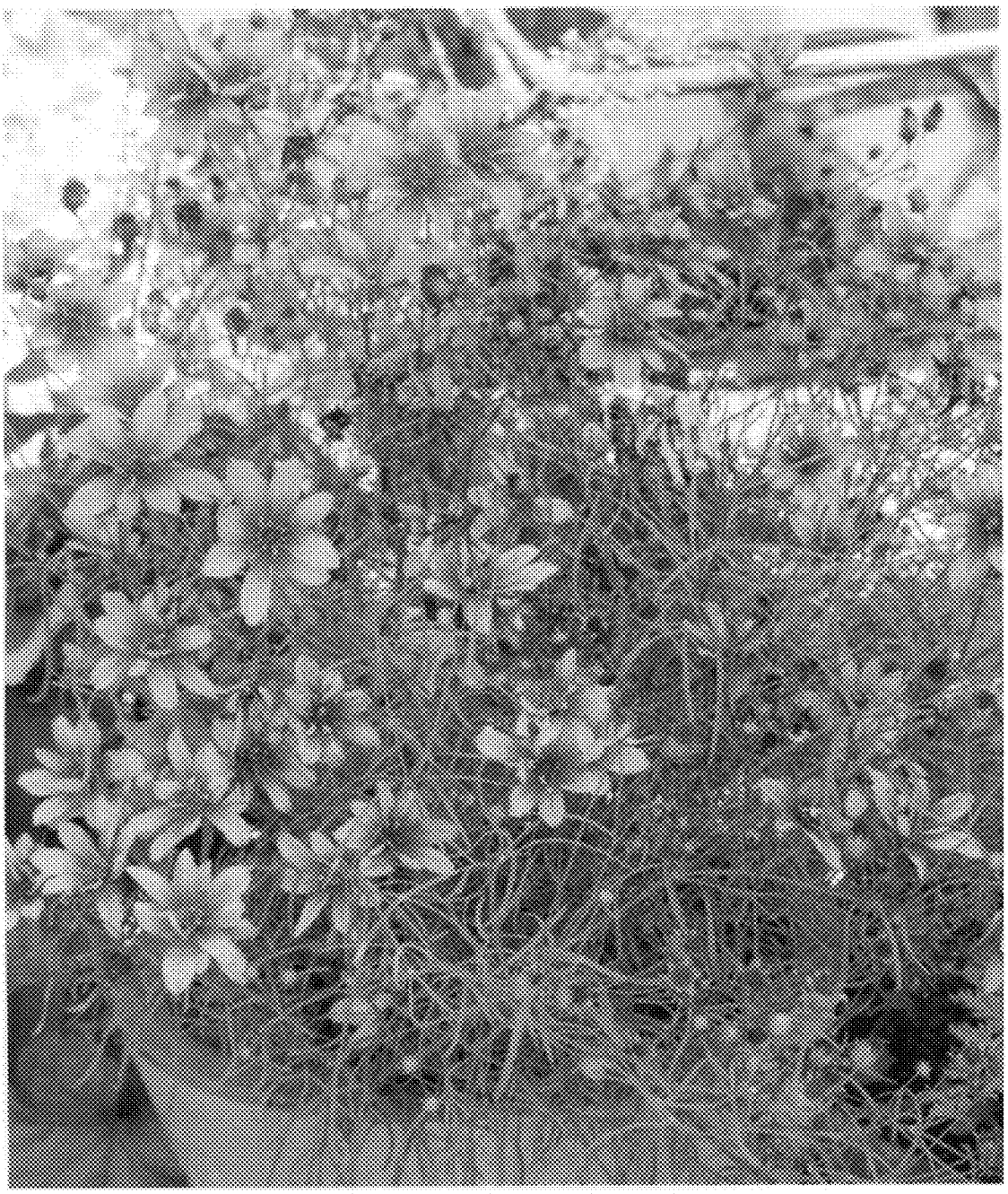

The photograph in FIG. 2 was taken of a one-year old plant of 'Sunset Strip' as grown outdoors in a two-gallon container and provides a view of the inflorescence color in summer. The Colors in the photograph may differ slightly from the color values cited in the detailed botanical description, which accurately describe the colors of the new *Coreopsis.*

DETAILED BOTANICAL DESCRIPTION

The following is a detailed description of the new cultivar as observed for three years in Pennsylvania and Georgia with the detailed data collected from plants grown outdoors for three months from a 72-cell plug in Alpharetta, Ga. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

*Blooming period*.—Blooms from June until Frost in Pennsylvania.

*Plant habit*.—Herbaceous annual, densely clump-forming with numerous basal branching to produce a bushy habit.

*Height and spread*.—Reaches a height of 45 to 50 cm (18 to 20 inches) and an average spread of 61 cm (24 inches).

*Diseases resistance*.—No particular resistance or susceptibility has been observed.

*Root description*.—Fibrous, fine and well-branched.

Growth and propagation:

*Propagation*.—Terminal stem cuttings.

*Growth rate*.—Vigorous and grows well under greenhouse conditions in winter.

Stem description:

*Shape*.—Round, solid.

*Stem color*.—146A to 146B.

*Stem size*.—An average of 22 cm in length and 2 mm in width.

*Stem surface*.—Glabrous, satin finish, slightly ridges.

*Branching habit*.—An average of 30 basal branches with laterals produced with pinching.

Foliage description:

*Leaf division*.—Simple, deeply incised, 5-lobed.

*Leaf margins*.—Entire.

*Leaf size*.—Up to 8 cm in length and 7 cm in width, lobes an average of 3 cm in length and 2 mm in width.

*Leaf shape*.—Fan shaped overall, lobes narrowly linear.

*Leaf base*.—Attenuate.

*Leaf apex*.—Acute.

*Leaf venation*.—Pinnate, not prominent, matches leaf color on both surfaces.

*Leaf attachment*.—Sessile.

*Leaf arrangement*.—Opposite.

*Leaf internode length*.—Average of 3 cm.

*Leaf quantity*.—An average of 8 per main stem.

*Leaf surface*.—Glabrous.

*Leaf color*.—New growth 144A, mature leaves 137B.

*Leaf fragrance*.—Faint and slightly sweet when crushed.

Flower description:

*Inflorescence type*.—Composite with ray florets surrounding disk florets in the center forming a radiant head, inflorescences are borne in groups of 2 to 3 at upper nodes and in groups of 3 at terminal.

*Lastingness of inflorescence*.—About one week until senescence of ray flowers, bracts and disk flowers are persistent.

*Fragrance*.—None detected.

*Quantity of inflorescences*.—An average of 8 per stem.

*Inflorescence size*.—An average of 2 cm in depth and up to 4 cm in diameter with disk portion an average of 7 mm in diameter.

*Inflorescence buds*.—Average of 9 mm in depth and 6 mm in diameter, shape is ovoid, color is 144B suffused with 199C with apex 7A.

*Peduncle*.—Average of 3.5 cm in length and 1 mm in diameter, 137B in color, glabrous surface.

Involucral bracts:

*Bract number*.—Two rows of 6 typically.

*Bract arrangement*.—Outer bracts are un-fused spreading and held at 45° from perpendicular, inner bracts overlap and surround receptacle with a campanulate form and held close to ray florets with apical portion spreading outward.

*Bract size*.—Outer bracts about 8 mm in length and 1 mm in width, inner bracts about 8 mm in length and 4 mm in width with free portion an average of 4 mm in length and 25 mm in width.

*Bract color*.—Outer bracts 137A with thin margin of 145A (both surfaces), inner bracts 137A and blending to N144A at apex (both surfaces).

*Bract texture*.—Outer bracts glabrous and satiny on both surfaces, inner bracts glabrous and waxy on both surfaces.

*Bract apex*.—Acute (inner and outer).

*Bract base*.—Truncate (inner and outer).

*Bract shape*.—Outer bracts linear, inner bracts broadly ovate.

Ray florets (sterile):

*Number*.—8.

*Shape*.—Elliptic to slightly obovate, most typically with 1 ligulate petal (petaloid pistil) approximately 6 mm in length and 2 mm in width.

*Size*.—Average of 2 cm in length and 9 mm in width.

*Apex*.—Slightly emarginated to slightly mucronate.

*Base*.—Broadly cuneate.

*Margins*.—Entire.

*Aspect*.—Held nearly horizontal to slightly upward, slightly wavy with apex slightly curled downward.

*Surface*.—Glabrous and ridged on both surfaces.

*Color*.—Upper surface opening and fully open; 17A and heavily suffused with 46A (eye zone) at base with vertical stripes spreading outward towards petal tip, the degree of spreading of 46A coloration is greater in fall, lower surface opening and fully open; 117C with fine vertical stripes of 177A.

Disk flowers (male and female):

*Number*.—Numerous, about 150.

*Shape*.—Tubular, corolla is fused, flared at apex.

*Size*.—About 6 mm in length and 2 mm in width.

*Color*.—In masse; 183C with stigmas 12A, corolla; 11C and translucent with apex 183A.

*Receptacle*.—About 4 mm in diameter and 2 mm in depth, 147A in color.

Reproductive organs:

*Presence*.—Disk flowers are perfect, ray flowers are sterile (often with petaloid pistil).

*Gynoecium*.—1 Pistil, 2.5 mm in length, style is very fine and about 160A in color and translucent, bifid pilose stigma is 12A in color with branches about 0.7 mm in length and recurved, ovary is 15 mm in length, 0.75 mm in width, inferior, and 11C in color.

*Androcoecium*.—5 stamens, fused into tube surrounding style, 1.5 mm in length and 0.3 mm in width, about 200A in color, no pollen was observed.

*Fruit*.—No fruit development has been observed.

It is claimed:

1. A new and distinct cultivar of *Coreopsis* plant named 'Sunset Strip' as herein illustrated and described.

* * * * *